United States Patent
Wu et al.

(10) Patent No.: US 7,356,113 B2
(45) Date of Patent: Apr. 8, 2008

(54) TOMOSYNTHESIS IMAGING SYSTEM AND METHOD

(75) Inventors: Tao Wu, Woburn, MA (US); Alex Stewart, Waltham, MA (US); Martin Stanton, Stow, MA (US); Walter Phillips, Arlington, MA (US); Daniel B. Kopans, Waban, MA (US); Richard Moore, Concord, MA (US)

(73) Assignee: Brandeis University, Waltham, MA (US)

( * ) Notice: Subject to any disclaimer, the term of this patent is extended or adjusted under 35 U.S.C. 154(b) by 254 days.

(21) Appl. No.: 10/776,690

(22) Filed: Feb. 11, 2004

(65) Prior Publication Data

US 2005/0105679 A1 May 19, 2005

Related U.S. Application Data

(60) Provisional application No. 60/446,784, filed on Feb. 12, 2003.

(51) Int. Cl.
*A61B 6/02* (2006.01)
(52) U.S. Cl. .......................... 378/27; 378/22
(58) Field of Classification Search .............. 378/4, 378/8, 15, 22, 901, 21, 27, 37
See application file for complete search history.

(56) References Cited

U.S. PATENT DOCUMENTS

| | | | |
|---|---|---|---|
| 5,270,926 A * | 12/1993 | Tam | 378/4 |
| 5,909,476 A * | 6/1999 | Cheng et al. | 378/4 |
| 6,002,739 A | 12/1999 | Heumann | |
| 6,256,370 B1 | 7/2001 | Yavuz | |
| 6,292,530 B1 | 9/2001 | Yavus et al. | |
| 6,480,565 B1 * | 11/2002 | Ning | 378/37 |
| 6,483,890 B1 * | 11/2002 | Malamud | 378/22 |
| 6,724,856 B2 * | 4/2004 | De Man et al. | 378/62 |
| 6,744,848 B2 * | 6/2004 | Stanton et al. | 378/55 |

OTHER PUBLICATIONS

Wu, Tao, Three-Dimensional Mammography Reconstruction Using Low Dose Projection Images [online], Sep. 2002. Retrieved from the Internet: <URL: http://proquest.umi.com/pqdweb?did=726427671&sid=1&Fmt=2&clientId=19649&RQT=309&VName=PQD>.*

(Continued)

*Primary Examiner*—Chih-Cheng G Kao
(74) *Attorney, Agent, or Firm*—Nutter, McClennen & Fish, LLP

(57) ABSTRACT

A system for three-dimensional tomosynthesis imaging of a target element includes an image acquisition element and a processor. The image acquisition element obtains a plurality of images of the target element from a plurality of angles and includes a radiation source that is positionable at a plurality of angles with respect to the target element and a radiation detector. The radiation detector is positioned so as to detect radiation emitted by the radiation source passing through the target element and determine a plurality of attenuation values for radiation passing through the target element to establish a radiation absorbance projection image of the target element for a particular radiation source angle. The processor is configured to apply an iterative reconstruction algorithm to the radiation absorbance projection images of the target element obtained from a plurality of radiation source angles to generate a three-dimensional reconstruction of the target element.

34 Claims, 6 Drawing Sheets

OTHER PUBLICATIONS

Browne, J.A. et al., "Developments with Maximum Likelihood X-Ray Computed Tomography," *IEEE Trans. on Med. Imaging* 11(1):40-52 (1992).

Chlewicki, W. et al., "Cone Based 3D Reconstruction: A FDK-SART Comparison For Limited Number of Projections," Dept. of Physics, Univ. of Patras, Greece.

Lange, K. et al., "A Theoretical Study of Some Maximum Likelihood Algorithms for Emission and Transmission Tomography," IEEE Trans. on Med. Imaging MI-6(2):106-114 (1987).

Niklason, L.T. et al., "Digital Tomosynthesis in Breast Imaging," Radiology 205(2):399-406 (1997).

Ollinger, J.M., "Maximum Likelihood Reconstruction of Transmission Images in Emission Computed Tomography via the EM Algorithm," IEEE Trans. on Med. Imaging 13(1):89-101 (1994).

Politte, D.G. et al., "The Use of Constraints to Eliminate Artifacts in Maximum-Likelihood Image Estimation for Emission Tomography," IEEE Trans. on Nuclear Sci. 35(1):608-610 (1988).

Suryanarayanan, S. et al., "Comparison of Tomosynthesis Methods Used with Digital Mammography," Acad. Radiol. 7:1085-1097 (2000).

Rockmore, A.J. et al., "A Maximum Likelihood Approach to Transmission Image Reconstruction from Projections," IEEE Trans. on Nuclear Sci. NS-24(3):1929-1935 (1977).

Wu, T., "Three-Dimensional Mammography Reconstruction Using Low-Dose Projection Images," Dissertation Brandeis Univ. (Sep. 2002).

* cited by examiner

TOMOSYNTHESIS IMAGING SYSTEM AND METHOD

RELATED APPLICATIONS

This application claims priority to provisional application Ser. No. 60/446,784, filed Feb. 12, 2003 and entitled Tomosynthesis Imaging System and Method, which is incorporated by reference herein.

STATEMENT REGARDING FEDERALLY SPONSORED RESEARCH

The research that led to this invention received sponsorship from the National Institutes of Health under contract/grant #s CA 66232 and RR 12598.

BACKGROUND OF THE INVENTION

1. Technical Field of the Invention

The present invention relates to a system and method for imaging a target element using tomosynthesis. More specifically, the invention relates to a system, method and computer program product for creating a three-dimensional image of target elements from a plurality of radiation absorbance projection images taken from different angles.

2. Background

Imaging of a patient's tissue has become a common screening and/or diagnostic tool in modern medicine. One example of such imaging is mammography, or the imaging of a patient's breast tissue. Breast cancer remains the most common cancer among women today, however, at this time there is no certain way to prevent breast cancer and the best strategy for dealing with breast cancer is early detection of the cancer so that it may be treated prior to metastatic spread. Accordingly, it is important for patients to have access to imaging techniques and systems that will detect very small cancers as early in their development as possible.

Conventional mammography involves an x-ray examination of the breast, typically using a fluorescent panel that converts transmission x-rays from a breast into visible light photons that expose a film. While screening using conventional mammography has been shown to reduce breast cancer deaths by approximately 30 to 50%, this imaging technique lacks the dynamic range that would allow it to detect small or hidden cancers, and thus permit therapy that can improve survival rates further. In particular, conventional mammography techniques suffer from the limitation that three-dimensional anatomical information is projected onto a two dimensional image. Because of this, "structure noise" such as overlapping breast tissues makes it difficult to perceive and characterize small lesions. This can result in a 10 to 30% false-negative diagnosis rate, especially where the cancer is masked by overlying dense fibroglandular tissue.

A three-dimensional approach to imaging could allow for the separation of overlying tissue and thus improve correct diagnosis rates for diseases such as breast cancer; however, three-dimensional imaging has not yet been applied for this purpose in the general population. The most widely used three-dimensional x-ray imaging technique is computed tomography ("CT"). A CT scanner contains a rotating frame that has one or more x-ray tubes mounted on one side and one or more detectors on the opposite side. As the rotating frame spins both the x-ray tube and the detector around the patient, numerous projections of the x-ray beam attenuated by a cross section slice of the body are acquired. These projections are then used to reconstruct cross-sectional images of the body. Despite the fact that CT has been found useful in detecting lesions in the breast, it is not suitable as a technique for regular breast imaging due to the high dose required to take a number of projections (approximately 100 to 1,000 projections) and the low spatial resolution (on the order of a millimeter). In addition, the CT projections mix attenuation effects from other organs of the body (such as those within the chest cavity) with the attenuation of the breast, which can distort information about the breast and causes these interposed organs to be irradiated. Still further, the cost of CT scanning is too high to permit its use as part of an annual exam.

A three-dimensional imaging approach called "tomosynthesis" has also been developed. Tomosynthesis is a technique that allows the reconstruction of tomographic planes on the basis of the information contained in a series of projections acquired from a series of viewpoints about the target object. They need not be regularly spaced, numerous, or arranged in any regular geometry. The tomosythesis technique is promising in that it may provide improved spatial differentiation of nearby tissues at very high resolution comparable to projection 2D imaging, with limited radiation. The problem of 3D reconstruction from tomosynthesis projections has been described as intractable by those skilled in the art.

In order for a three-dimensional imaging technique to be successful in medical diagnosis and other applications, it should offer:

Sufficient spatial resolution and contrast resolution to detect and characterize, for example, breast cancers;
Minimum radiation dose to a patient;
Fast image acquisition;
Cost effectiveness; and
3D reconstruction that can be performed effectively.

SUMMARY OF THE INVENTION

In one aspect, the invention provides a method that enables to the use of tomosynthesis to efficiently provide accurate three-dimensional imaging of a target element. This method involves acquiring radiation absorbance images of the target element through a limited plurality of angles and applying an iterative reconstruction algorithm to generate the three-dimensional reconstruction of the target element. This method can gain further accuracy where the iterative reconstruction algorithm is applied using cone beam forward projection and back projection.

In a further aspect of the invention, a system for three-dimensional tomosynthesis imaging of a target element is provided having an image acquisition element and a processor. The image acquisition element obtains a plurality of images of the target element from a plurality of angles and includes a radiation source that is positionable at a plurality of angles with respect to the target element and a radiation detector. The radiation detector is positioned so as to detect radiation emitted by the radiation source passing through the target element and determine a plurality of attenuation values for radiation passing through the target element to establish a radiation absorbance projection image of the target element for a particular radiation source angle. The processor is configured to apply an iterative reconstruction algorithm to the radiation absorbance projection images of the target element obtained from a plurality of radiation source angles to generate a three-dimensional reconstruction of the target element. Again, the system can gain further accuracy where the iterative reconstruction algorithm is applied using cone-beam forward projection and back projection.

In a still further aspect of the invention, a computer program for three-dimensional tomosynthesis imaging of a target element is provided. The three-dimensional images are created from a plurality of radiation absorbance projection images obtained at different angles from an image acquisition element having a radiation source positionable at a plurality of angles with respect to the target element and a radiation detector. The radiation detector is positioned so as to detect radiation emitted by the radiation source passing through the target element and determine a plurality of attenuation values for radiation passing through the target element to establish a radiation absorbance projection image of the target element for a particular radiation source angle. The computer program code is embodied in a computer readable medium and includes computer program code for applying an iterative reconstruction algorithm to the radiation absorbance projection images of the target element obtained from a plurality of radiation source angles to generate the three-dimensional reconstruction of the target element wherein the iterative reconstruction algorithm is applied using cone-beam forward projection and back projection.

In specific embodiments of any of these aspects of the invention, the radiation absorbance images can be acquired by transmitting x-ray energy from an x-ray source through the target element to an x-ray detector and the x-ray detector may have a plurality of detector pixels. The three-dimensional reconstruction of the target element may be represented as an array of voxels having a uniform or non-uniform size in three-dimensions. The forward projection step may then be implemented by ray tracing from the x-ray source to a detector pixel and the forward projection of the target element is obtained by repeating the ray tracing for each detector pixel to calculate an attenuation value for each voxel. The back projection step can be implemented by locating detector pixels containing attenuation information relating to a selected voxel and using those pixels to update the attenuation value of the selected voxel. The back projection step can further include performing a back projection for at least each voxel corresponding to a three-dimensional reconstruction of the target element. In the enumerated aspects of the invention or in any of their embodiments, the iterative reconstruction algorithm may be a maximum likelihood algorithm and the maximum likelihood estimation can be implemented using an expectation-maximization algorithm.

The invention is particularly useful for creating three-dimensional reconstructions of animal and more particularly human tissue. In one preferred embodiment, the invention is employed in mammography to create a three-dimensional reconstruction of the breast tissue of a human female patient.

BRIEF DESCRIPTION OF THE DRAWINGS

The invention will be more fully understood from the following detailed description taken in conjunction with the accompanying drawings.

DETAILED DESCRIPTION OF THE INVENTION

The systems and methods of the present invention address the needs of the art by providing tomosynthesis apparatus and techniques for imaging target elements that overcome the problems of conventional three-dimensional imaging systems. The present invention enables the use of tomosynthesis to efficiently provide accurate three-dimensional imaging of a target element in which overlapping sub-elements having differing attenuation characteristics by applying a 3D reconstruction algorithm having a novel combination of features. The algorithm can employ a cone-beam geometry lacking in geometric simplification such as parallel-beam based approximation methods. The algorithm can further apply the cone-beam geometry in an iterative forward-projection and back-projection method based on maximum-likelihood image estimation using an estimation-maximization algorithm. The invention is applied below to one preferred embodiment in which the system is used for tomosynthesis mammography; however, the invention will be useful in a variety of three-dimensional imaging situations. For example, the invention can be applied to a variety of patient imaging problems such as heart imaging, or imaging of the soft tissues or bones of the hand. The imaging system of the invention can be used for diagnoses (as is described below for tomosynthesis mammography) or it may be used for other applications such as three-dimensional modeling for the purpose of fitting an implant (whether orthopedic, such as a hip or knee implant, an artificial heart, or other type of implant) or for use in surgical navigation systems. What follows is a description of one preferred embodiment of the invention.

1. Tomosynthesis Mammography System

Figure 1:
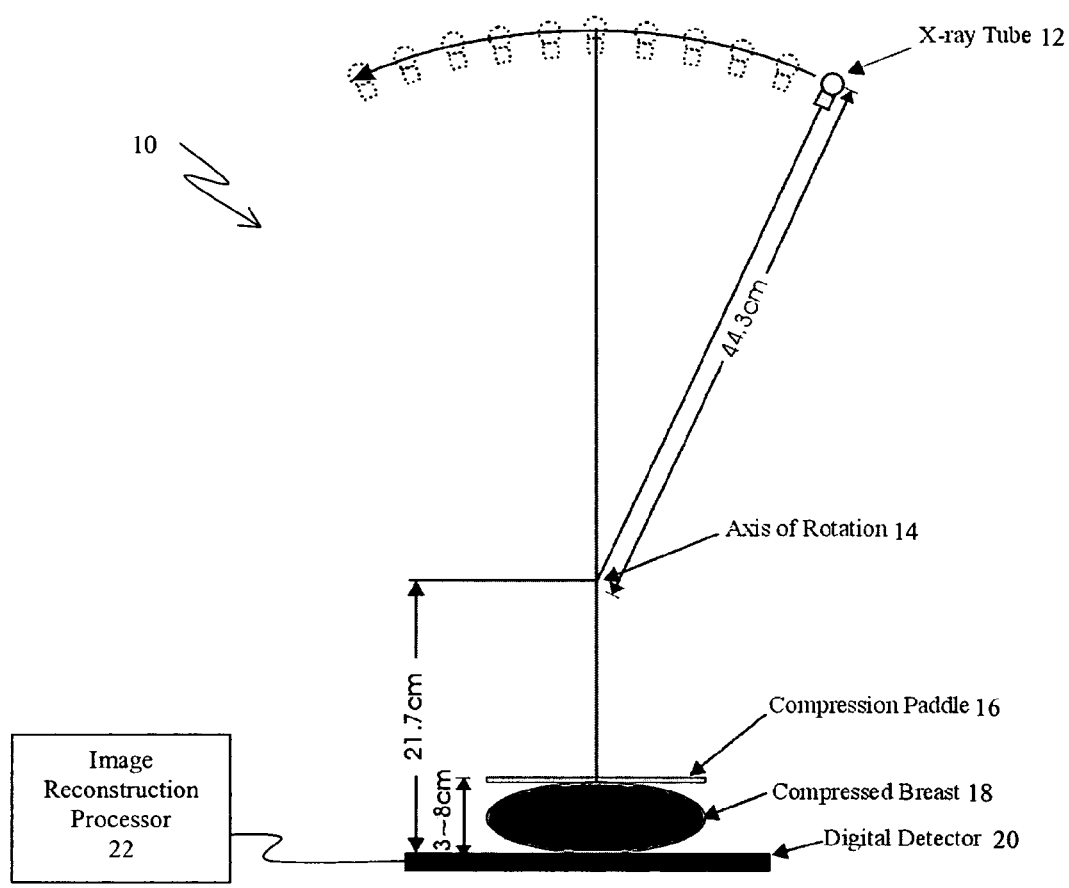
FIG. 1 is a diagram illustrating the geometry of a tomosynthesis system of the invention.

Tomosynthesis mammography is a three-dimensional breast imaging technique. It involves acquiring projection images of a breast at a plurality of viewpoints, typically over an arc or linear path. Three-dimensional distribution of x-ray attenuation coefficient of the breast volume is reconstructed from these projections. A prototype tomosynthesis system 10 for breast imaging is illustrated in FIG. 1. In this exemplary system, eleven projections are acquired by moving the x-ray tube 12 over a 50° arc (−25° to +25°) above the target element, in this case breast tissue 18 which may be compressed by compression paddle 16, in 5° angular steps about axis of rotation 14. Breast tissue 18 and digital detector 20 are stationary during the image acquisition. Certain characteristics of this exemplary embodiment of a tomosynthesis system of the invention are described below:

Spatial resolution and contrast resolution: The tomosynthesis system uses an amorphous-Silicon-based flat panel digital detector 20 on which a CsI crystal phosphor is grown epitaxially. It reads out 2304×1800 pixels (100 µm pixel pitch) via a TFT array. The detector has a linear response over exposure levels up to 4000 mR and 12 bits of working dynamic range. Each plane of the 3D reconstruction has about the same resolution as the detector (100 um) but the depth resolution is on the order of a millimeter.

Dose: The target/filter combination is Rh/Rh and the accelerating potential is 25~33 kVp to image breasts with 3~8 cm range of thickness. The total x-ray dose for acquiring 11 projections is approximately 1.5 times of that used for one film-screen mammogram. Each projection is a low dose breast image (approximately 1/11 of the does per projection).

Patient motion: Patient motion is reduced by fast image acquisition. Using cone-beam x-ray geometry and area detector, a projection of the whole breast can be recorded with one x-ray exposure at each angle. For each projection, the exposure time is 0.1–0.2 s and detector readout time is about 0.3 s. Rotation to the next angle is performed during the detector readout. The total image acquisition time for 11 projections is about 7 sec. Breast compression also helps to reduce patient motion.

Image acquisition geometry: The design of the tomosynthesis system can be based on the conventional mammography system. The MLO views have been used in most cases since it provides the most complete coverage of the whole breast.

2. 3D Reconstruction Algorithm

Tomosynthesis can take advantage of the high efficiency of a digital detector in acquiring low dose breast images. Prior to the present invention, appropriate reconstruction methods that make good use of the low dose projections and the acquisition geometry of the tomosynthesis system 10 have not been deployed. For an initial evaluation, Niklason implemented a "shift-and-add" method that is similar to backprojection [Niklason et al, 1997]. Methods used by others [Chakraborty et al, 1984; Haaker et al, 1985; Suryanarayanan et al, 2000] essentially did not handle the limited statistics in low dose projection images. In theory, they were not suitable in the case of limited number of projections and limited angular range. Therefore, the three-dimensional information extracted by these methods was limited, which resulted in poor quality reconstructions.

The Maximum Likelihood (ML) algorithm is an iterative reconstruction method [Rockmore, 1977; Shepp et al, 1982; Levitan et al, 1987; Herbert et al, 1989; Browne et al, 1992; Manglos et al, 1995; Pan et al 1997; Zhou et al, 1997]. It is well suited for tomosynthesis reconstruction, which is an ill-conditioned problem (only 11 low dose projections are available). The ML algorithm incorporates the stochastic nature of the x-ray transmission process so that the statistical noise in projection images is taken into consideration in the case of low x-ray flux. It also incorporates the information of the object into the reconstruction in the form of constraints.

In ML reconstruction, the Likelihood function, which is the probability of obtaining the projections Y obtained in a measurement, given a certain model for the three-dimensional map of attenuation coefficients u is:

$$L = P(Y|u) \quad (1)$$

The ML solution is the 3D reconstruction that maximizes the probability of the measured projections. Because an analytical solution is usually intractable, an iterative algorithm is a better choice. The incident and transmitted x-rays follow Poisson statistics and the log-likelihood is described by:

$$LnL = \sum_i (-N_i e^{-\langle l, u \rangle_i} - Y_i \langle l, u \rangle_i + Y_i \ln N_i - \ln Y_i) \quad (2)$$

where u is the linear attenuation coefficient; $N_i$ is the number of incident x-ray photons to projection pixel i, before attenuation; $Y_i$ is the number of transmitted x-ray photons to projection pixel i, after attenuation; $l_{ij}$ is the path length of beam ray i in the object (reconstruction voxel j; and $$\langle l, u \rangle_i = \sum_j l_{ij} u_j$$

is the total attenuation along beam ray to pixel i.

The algorithm by Lange and Fessler [Lange and Fessler, 1995] can be selected to solve the ML problem. At the n-th iteration, the value of an object voxel μ is updated by:

$$u_j^{(n+1)} = u_j^{(n)} + u_j^{(n)} \frac{\sum_i l_{ij}(N_i e^{-\langle l, u^{(n)} \rangle_i} - Y_i)}{\sum_i (l_{ij} \langle l, u^{(n)} \rangle_i N_i e^{-\langle l, u^{(n)} \rangle_i})} \quad (3)$$

where the notations are the same as above.

3. Implementation of the Cone-Beam Reconstruction

Cone-beam forward projection and back projection can form the basis for iterative reconstruction according to the invention. At the forward projection step, the projection images at 11 angles are calculated based on the current 3D reconstruction model. At the backprojection step, the calculated projections and the measured projections are compared and the 3D reconstruction model is updated according to their difference.

The forward projection to a detector pixel i at a projection angle can be used to illustrate the whole forward projection problem. An x-ray beam containing $N_i$ photons is incident from the source to the center of the selected detector pixel. This beam penetrates a series of object voxels and is sequentially attenuated by them. The total aggregate attenuation is $\langle l, u^{(n)} \rangle_i$ and the number of transmitted photons is $N_i e^{-\langle l, u^{(n)} \rangle_i}$, which is the forward projection to the pixel. This operation is repeated for all detector pixels that form the forward projection at this angle. The forward projections at all angles can be done in the same way except that the "pseudo-beam" is rotated.

The 3D reconstruction model is updated at the backprojection step. Equation 3 describes the update of a voxel j at the n-th iteration of reconstruction. The whole image is updated by doing the same operation on every voxel in it. At a projection angle, the center of the voxel is projected from the source to a detector pixel containing the attenuation information of this voxel. This operation is repeated at other angles and totally 11 detector pixels are found. In equation 3, the values of these 11 pixels, both in forward projection and in measured projection are used to update the object (reconstruction) voxel (the summation is on the set of these 11 pixels).

3.1 Positions of X-Ray Source, Object Voxel and Detector Pixel

Figure 2:
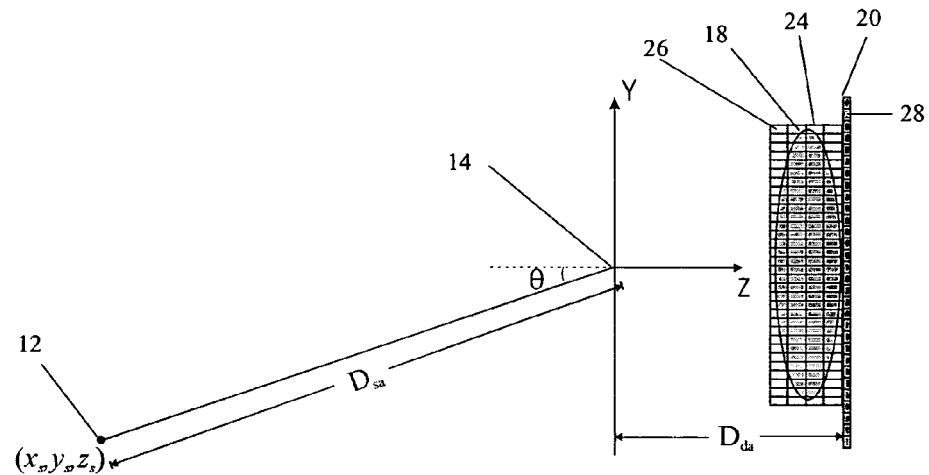
FIG. 2 is a top view of the coordinate system of a tomosynthesis system of the invention.

The origin of the coordinate system is at the axis of rotation 14 as illustrated in FIG. 2. The rotation plane of the x-ray 12 source is the YZ-plane (x=0). The detector 20 is parallel to the XY-plane at z=21.7 cm. The distance between the source 12 and the axis of rotation 14 is $D_{sa}$ and the distance between the detector 20 and the axis of rotation 14 is $D_{da}$. At projection angle θ, the position of the x-ray source 12 is:

$$x_s(\theta) = 0$$

$$y_s(\theta) = D_{sa} \cdot \sin(\theta)$$

$$z_s(\theta) = -D_{sa} \cdot \cos(\theta) \qquad (4)$$

The reconstructed object 24 is a rectangular volume, represented by a three-dimensional array of voxels 26. The breast volume 18 is contained in this rectangular volume 24. In a reconstructed image, the value of a voxel is positive if it represents breast tissue; zero if it represents the empty space out of the breast. In the coordinate system, the position of a voxel 26 indexed by ($m_x$, $m_y$, $m_z$) is:

$$x_{obj} = X_{obj} + m_x \cdot d_x$$

$$y_{obj} = Y_{obj} + m_y \cdot d_y$$

$$z_{obj} = Z_{obj} + m_z \cdot d_z \qquad (5)$$

where ($X_{obj}$, $Y_{obj}$, $Z_{obj}$) is the position of the center of the rectangular volume 24; $d_x$, $d_y$ and $d_z$ are the size of the voxel 26 in three dimensions.

The position of a detector pixel 28 indexed by ($n_x$, $n_y$) is:

$$x_p = X_p + n_x \cdot d'_x$$

$$y_p = Y_p + n_y \cdot d'_y$$

$$z_p = D_{da} \qquad (6)$$

where ($X_p$, $Y_p$) is the position of the center of the detector 20; $d'_x$ and $d'_y$ are the size of the pixel 28 in X and Y dimensions.

3.2 Forward Projection

The forward projection is implemented by ray tracing from the x-ray source 12 to detector pixel 28. At a projection angle, the x-ray beam to a detector pixel 12 is attenuated from the point where the beam enters the volume 24 to the point where it goes out. The total attenuation along the beam $\langle \iota, u^{(n)} \rangle_i$ is calculated by accumulating the attenuation $\iota \cdot u^{(n)}$ by each voxel 26 on the beam line. The number of transmitted x-rays to the pixel 28 is $N_t e^{-\langle \iota, u^{(n)} \rangle_i}$. The forward projection of the object 18 at this angle is obtained by repeating this operation for all detector pixels 28. The forward projections at other angles are calculated in the same way except the x-ray source 12 is at a different location.

Figure 3:
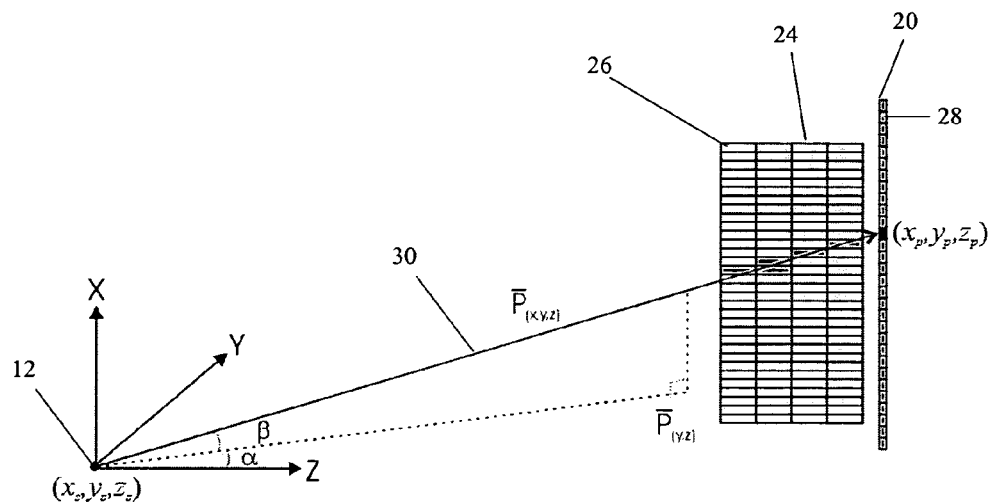
FIG. 3 illustrates a forward projection of the tomosynthesis system of the invention.

The first step of forward projection is to determine the orientation of the x-ray beam 30 as illustrated in FIG. 3. At an angle, the position of the x-ray source ($x_s$, $y_s$, $z_s$) 12 and detector pixel ($x_p$, $y_p$, $z_p$) 28 are determined by equation 4 and 6. The orientation of the beam $\vec{P}_{(x,y,z)}$ 30 from source 12 to the detector pixel 28 can be described by two parameters: (1) β, the angle made by the beam and the YZ-plane; (2) α, the angle made by the projection of the beam in YZ-plane and the Z-axis. These two parameters are determined by:

$$\alpha = \tan^{-1}((y_p - y_s)/(z_p - z_s)) \qquad (7)$$

$$\beta = \tan^{-1}\left(x_p \Big/ \sqrt{(y_p - y_s)^2 + (z_p - z_s)^2}\right)$$

Figure 4:
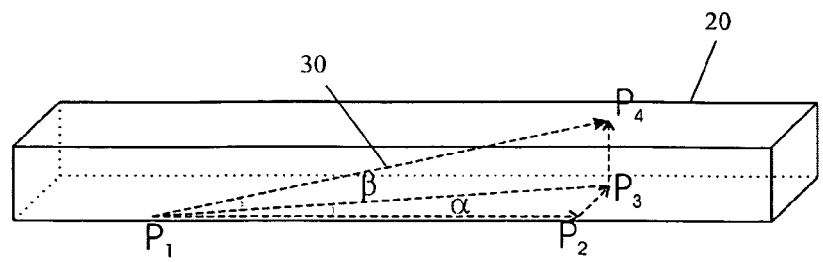
FIG. 4 illustrates the path length of an x-ray beam in a voxel in the tomosynthesis system of the invention.

The path length $|\overrightarrow{P_1 P_4}|$ of the x-ray beam 30 through a voxel 26, as illustrated in FIG. 4, is also the distance between the centers of two successive voxels along the beam. The position of the next voxel along the beam can be located by shifting Δx, Δy and Δz ($\overrightarrow{P_1 P_2}$, $\overrightarrow{P_2 P_3}$ and $\overrightarrow{P_3 P_4}$ in FIG. 4) along three dimensions from the current voxel 26.

$$\Delta x = \overrightarrow{P_1 P_2} = \overrightarrow{P_1 P_4} \cdot \cos \beta \cdot \cos \alpha$$

$$\Delta y = \overrightarrow{P_1 P_2} = \overrightarrow{P_1 P_4} \cdot \cos \beta \cdot \cos \alpha$$

$$\Delta z = \overrightarrow{P_1 P_2} = \overrightarrow{P_1 P_4} \cdot \sin \beta \qquad (8)$$

Figure 5:
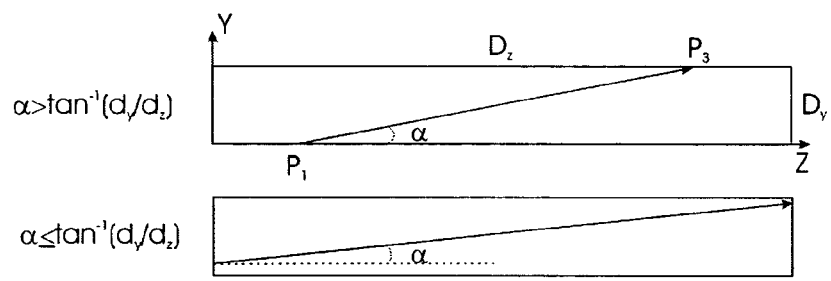
FIG. 5 illustrates a projection of the path length of FIG. 4.

To calculate $|\overrightarrow{P_1 P_4}|$ its projection in the YZ-plane $\overrightarrow{P_1 P_3}$, illustrated in FIG. 5, is calculated first:

$$|\overrightarrow{P_1 P_3}| = d_y / \sin\alpha \quad \text{if } a > \tan^{-1}(d_y / d_z); \qquad (9)$$

$$|\overrightarrow{P_1 P_3}| = d_z / \cos\alpha \quad \text{if } a \le \tan^{-1}(d_y / d_z)$$

In a similar way, the path length $|\overrightarrow{P_1 P_4}|$ can be calculated by:

$$|\overrightarrow{P_1 P_4}| = d_x / \sin\beta \quad \text{if } \beta > \tan^{-1}(d_x / |\overrightarrow{P_1 P_3}|); \qquad (10)$$

$$|\overrightarrow{P_1 P_4}| = d_x / \cos\beta \quad \text{if } \beta \le \tan^{-1}(d_x / |\overrightarrow{P_1 P_3}|)$$

Figure 6:
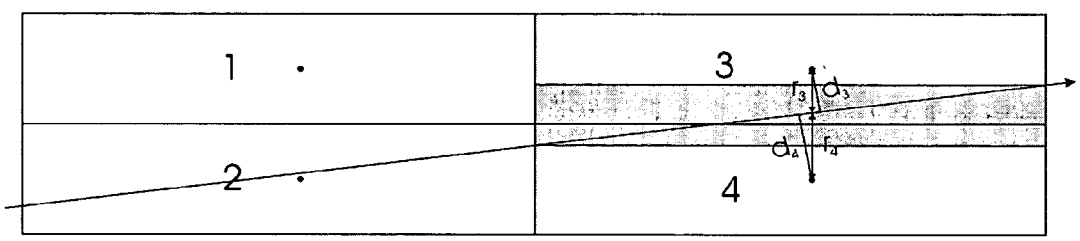
FIG. 6 illustrates an exception to the projection of FIG. 5.

There are exceptions to the two cases illustrated in FIG. 5. In a case shown in FIG. 6, the path lengths through voxel 3 and 4 cannot be described by equation 10. But the total path length of them is equal to the path length in voxel 2. The total attenuation by voxel 3 and 4 is equivalent to the attenuation by the shaded area in FIG. 6, which has the same path length as voxel 2. The equivalent attenuation is estimated by a linear interpolation of attenuations by voxel 3 and 4. The weighting for the interpolation is proportional to the inverse of the distance from the voxel center to the beam line. The ratio of the weighting for voxel 3 to that for voxel 4 is $d_4/d_3$, equivalent to $r_4/r_3$, where $d_3$ and $d_4$ are the distances from the voxel center to the beam; $r_3$ and $r_4$ are the distances from the voxel center to the projection of the beam along the Y-axis.

The total attenuation along a beam to a detector pixel i is the summation from the first voxel at the point where the beam enters the volume to the voxel at the point where the beam goes out of the volume. For a beam with orientation (α, β), the position of the voxel at entering point is:

$$x_0 = x_s + \sqrt{(y_0 - y_s)^2 + (z_0 - z_s)^2} \cdot \tan\beta \qquad (11)$$

$$y_0 = y_s + (z_0 - z_s) \cdot \tan\alpha;$$

$$z_0 = 21.7 - D;$$

where D is the thickness of the reconstruction volume. The attenuation $\iota \cdot u_0$ by the first voxel at ($x_0$, $y_0$, $z_0$) is calculated and then the tracing point is shifted forward by (Δx, Δy, Δz) to the next voxel along the beam, where the attenuation $\iota \cdot u_1$ is calculated and added to $\iota \cdot u_0$. At the n-th step, the position being search is:

$$x_n = x_0 + n \cdot \Delta x$$

$$y_n = y_0 + n \cdot \Delta y$$

$$z_n = y_0 + n \cdot \Delta z \qquad (12)$$

The number of steps of forward projection is V=int(D/Δz)+1. After V steps, the total attenuation along the beam to detector pixel i is $$\sum_{n=0}^{M} u_n \cdot l_n$$

(represented by $\langle \iota, u^{(n)} \rangle_i$). The number of transmitted x-ray photons is $$N_i e^{-\sum_{n=0}^{N} u_n \cdot l_n}.$$

3.3 Backprojection

Figure 7:
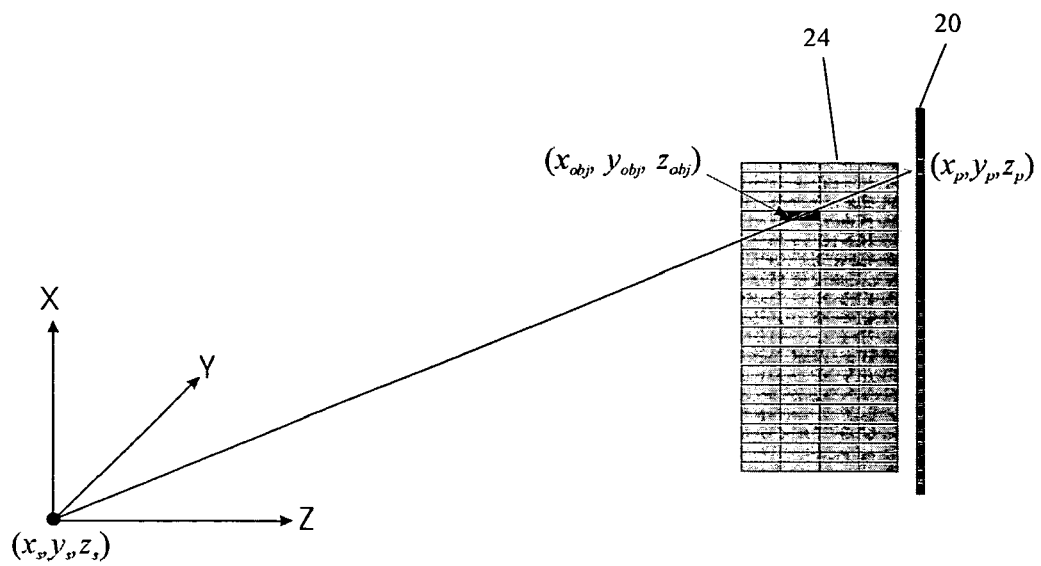
FIG. 7 illustrates a back-projection step of the invention.

The value of the object voxel is updated at the backprojection step as illustrated in FIG. 7. At this step, projection pixels containing the attenuation information of the selected object voxel are found and used to update the value of this voxel. At a projection angle, the position of the detector pixel ($x_p$, $y_p$, $z_p$) which contains the information of a selected voxel is:

$$x_p = x_s + (x_{obj} - x_s) \cdot (z_p - z_s)/(z_{obj} - z_s)$$

$$y_p = y_s + (y_{obj} - y_s) \cdot (x_p - x_s)/(x_{obj} - x_s)$$

$$z_p = 21.7 \quad (13)$$

where ($x_s$, $y_s$, $z_s$) is the position of the x-ray source at this angle. This operation is repeated to find detector pixels related to this voxel at other angles. The value of this voxel is updated by equation 3, using these detector pixels.

4. Image Reconstruction Results

4.1 Study on an ACR Phantom/Mastectomy Specimen

Figure 8A:
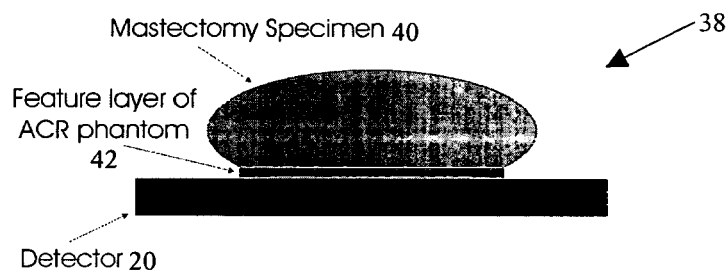
FIG. 8A illustrates a phantom used to test a system of the invention.
Figure 8B:
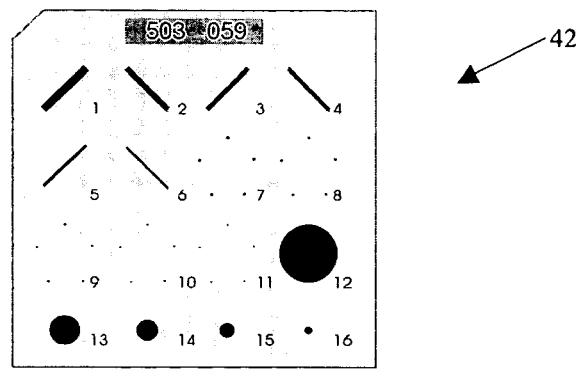
FIG. 8B illustrates a feature plate that makes up a portion of the phantom of FIG. 8A.

A phantom 38 is composed of a piece of mastectomy specimen 40 and a feature plate 42 from an American College of Radiology (ACR) accredited mammography phantom and placed on detector 20 as illustrated in FIG. 8A. The feature plate 42, further illustrated in FIG. 8B, contained nylon fibers (labeled 1 to 6 on the plate), simulated microcalcifications (labeled 7 to 11 on the plate) and tumor-like masses (labeled 12 to 16 on the plate). The mastectomy specimen 40 is a surgically removed breast tissue containing lesions. The combination of the feature plate 42 with the mastectomy specimen 40 makes it very hard to find features of the ACR phantom 42. The reconstructed feature plate demonstrates how the three-dimensional reconstruction works to improve the visibility of features.

Figures 9A, 9B, 9C:
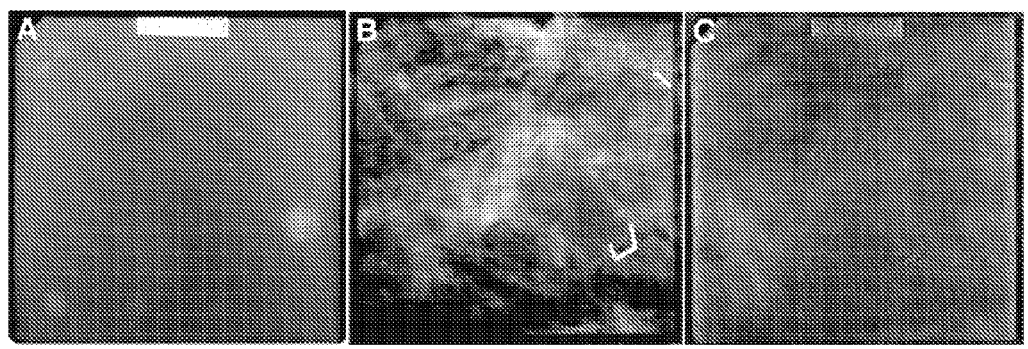
FIGS. 9A, 9B, and 9C illustrate structural noise reduction in (A) a projection of an ACR phantom; (B) a projection of a mastectomy specimen/ACR phantom; and (C) a reconstructed ACR phantom feature layer.

Ten features (fiber 1, 2, 3, 4; micro-calcification cluster 7, 8, 9 and mass 12, 13, 14) can be seen very well in a projection of the 4 cm thick ACR phantom 42 itself (Rh/Rh, 28 kVp and 160 mAs) as shown in FIG. 9A. With the superimposed mastectomy specimen 40, only one feature (micro-calcification cluster 7) is visible in a projection (Rh/Rh, 30 kVp and 140 mAs) as can be seen in FIG. 9B.

The reconstruction of the feature layer after 10 iterations is shown in FIG. 9C. The x-ray energy and exposure are the same as that used to create the image of FIG. 9B. More features (micro-calcification cluster 7, 8, 9 and mass 12) can be seen in the reconstruction. Even some low contrast features (fiber 1, 2, 3, 4) are recognizable. The number "503 059" on the label is clearer. It is clear that the visibility of features are significantly improved.

4.2 3D Reconstruction of a Patient Tissue

Clinical imaging of volunteers conducted at Massachusetts General Hospital under IRB approved protocols have been reconstructed for comparison of conventional film-screen mammography and to tomosynthesis mammography.

Figures 10A, 10B:
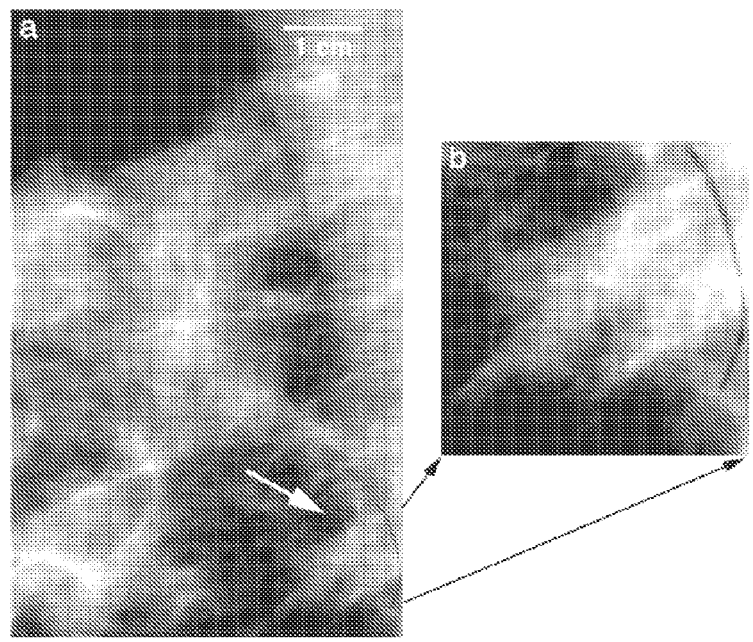
FIG. 10 is a film-screen mammogram of a patient's tissue.

As an example, a mediolateral oblique (MLO) mammogram from a volunteer was obtained using film-screen system (Mo/Mo, 25 kV and 330 mrad average glandular dose). The x-ray film image is shown in FIG. 10. The patient was found to have a non-palpable 10 mm invasive ductal cancer with associated in situ tumor and this was proved by biopsy. The cancer was difficult to see in the conventional screening mammogram and was found primarily because the calcifications associated with it drew the attention of the radiologist.

Figures 11A, 11B, 11C:
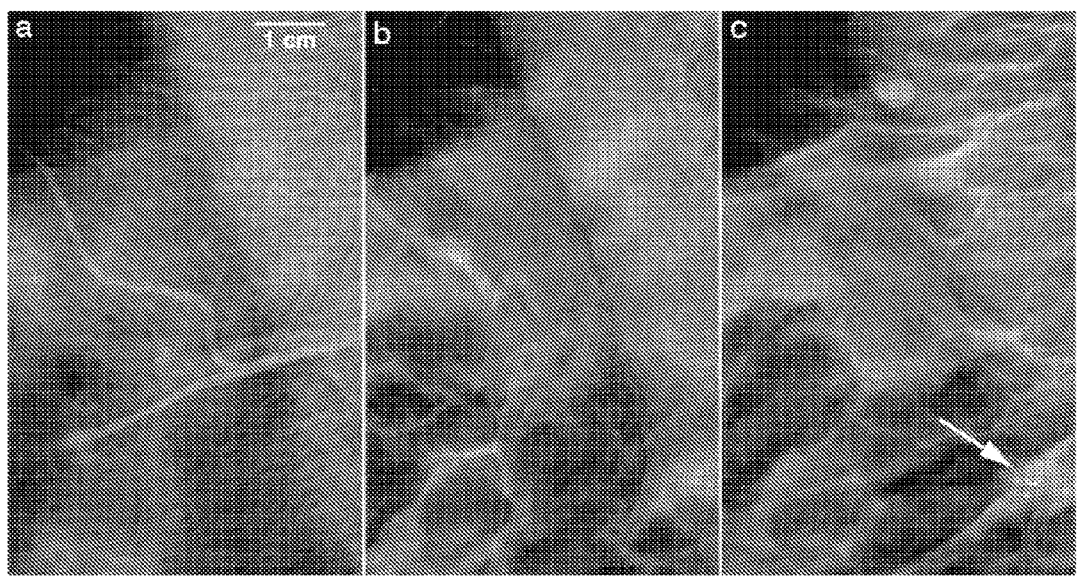
FIGS. 11A, 11B, and 11C illustrate slices of a reconstructed volume of the same tissue at three different depths.

A tomosynthesis image dataset was taken with Rh/Rh target/filter at 28 kVp and a total dose of 307 mrad. Three reconstructed slices from the 3D reconstruction are shown in FIG. 11. Blood vessels are seen near the breast skin in FIG. 11A. A tumor that has intraductal as well as invasive ductal cancer elements is just out of the plane of section in FIG. 11B. The invasive tumor mass, marked by an arrow, with associated calcifications in the in situ portion is clearly seen in FIG. 11C, as is a benign intramammary lymph node in the upper portion of the image.

It is apparent from this volunteer's dataset that overlapping structures in the conventional two-dimensional projection images (FIG. 10) were spacially separated. A reconstructed image provided at three different depths (FIG. 11A illustrating a depth of Z=2 mm, FIG. 11B illustrating a depth of Z=22 mm, and FIG. 11C illustrating a depth of Z=32 mm) makes it easier to see the tumor and calcifications and their relative geometry.

A person of ordinary skill in the art will appreciate further features and advantages of the invention based on the above-described embodiments. Accordingly, the invention is not to be limited by what has been particularly shown and described, except as indicated by the appended claims or those ultimately provided in a utility application claiming priority to this provisional application. A number of references have been referred to in the specification by last name of the first listed author and year of publication; those references are listed by full citation in the Bibliography below. All publications and references cited herein are expressly incorporated herein by reference in their entirety, in particular, each of the references listed in the Bibliography below is expressly incorporated for the teachings referred to in the sections of the application above for which they are cited.

BIBLIOGRAPHY

U.S. Pat. No. 5,872,828 to Niklason et al., entitled "Tomosynthesis System for Breast Imaging."

J. A. Browne, and T. J. Holmes, "Developments with Maximum Likelihood X-ray Computed Tomography," IEEE Transactions on Medical Imaging, 11 (1): 40-52 (1992).

D. P. Chakraborty, M. V. Yester, G. T. Barnes and A. V. Lakshminarayanan, "Self-masking subtraction tomosynthesis," Radiology, 150:225-229 (1984).

P. Haaker, E. Klotz, R. Koppe, R. Linde and H. Moller, "A New Digital Tomosynthesis Method With Less Artifacts for Angiography," Medical Physics, 12(4): 431-436 (1985).

T. J. Herbert and R. M. Leahy, "A Generalized EM Algorithm for 3-D Bayesian Reconstruction from Poisson Data Using Gibbs Priors," IEEE Transactions on Medical Imaging, 8(2): 194-202 (1989).

K. Lange and J. A. Fessler, "Globally Convergent Algorithm for Maximum a Posteriori Transmission Tomography," IEEE Transactions on Image Processing, 4: 1430-1438 (1995).

E. Levitan and G. T. Herman, "A Maximum A Posteriori Probability expectation Maximization Algorithm or Image Reconstruction in Emission Tomography," IEEE Transactions on Medical Imaging, MI-6(3): 185-192 (1987).

S. H. Manglos, G. M. Gagne, F. D. Thomas and R. Narayanaswamy, "Transmission Maximum-Likelihood Reconstruction with Ordered Subsets for Cone Beam CT," Physics in Medicine and Biology, 40: 1225-1241 (1995).

L. T. Niklason, B. T. Christian, L. E. Niklason, D. B. Kopans, D. E. Castleberry, B. H. Opsahl-Ong, C. E. Landberg, P. J. Slanetz, A. A. Giardino, R. M. Moore, D. Albagi, M. C. DeJule, P. A. Fitzgerald, D. F. Fobare, B. W. Giambattista, R. F. Kwasnick, J. Liu, S. J. Lubowski, G. E. Possin, J. F. Richotte, C-Y Weinad R. F. Wirth, "Digital Tomosynthesis in Breast Imaging," Radiology, 205: 399-406 (1997).

L. T. Niklason, B. T. Christian, L. E. Niklason, D. B. Kopans, P. J. Slanetz, D. E. Castleberry, B. H. Opsahl-Ong, C. E. Landberg, B. W. Giambattista, "Digital Breast Tomosynthesis: Potentially a New Method for Breast Cancer Screening," Digital Mammography, edited by N. Karssemeijer, M. Thijssen, J. Hendriks and L. van Erning, 13: 51-56 (Kluwer Academic Publishers, 1998).

T. Pan, B. M. W. Tsui and C. L. Byrne, "Choice of Initial Conditions in the ML Reconstruction of Fan-Beam Transmission with Truncated Projection Data," IEEE Transactions on Medical Imaging, 16(4): 426-438 (1997).

A. J. Rockmore and A. Macovski, "A Maximum Likelihood Approach to Transmission Image Reconstruction From Projections," IEEE Transactions on Nuclear Science, 24: 1929-1935 (1977).

L. A. Shepp and Y. Vardi, "Maximum Likelihood Reconstruction for Emission Tomography," IEEE Transactions on Medical Imaging, MI-1:113-122 (1982).

S. Suryanarayanan, A. Karellas, S. Vedantham, S. J. Glick, C. J. D'Orsi, S. P. Baker and R. L. Webber, "Comparison of Tomosynthesis Methods Used with Digital Mammography," Academic Radiology, 7:1085-1097, (2000).

Z. Zhou, R. M. Leahy and J. Qi, "Approximate Maximum Likelihood Hyperparameter Estimation for Gibbs Priors," IEEE Transactions on Image Processing, 6(6): 844-861 (1997).

What is claimed is:

1. An imaging method for creating a three-dimensional reconstruction of a target element comprising:
   acquiring radiation absorbance images of the target element by moving a radiation source through a limited plurality of angles;
   applying an iterative reconstruction algorithm to the radiation absorbance images to generate a three-dimensional reconstruction of the target element using tomosynthesis; and
   displaying at least a portion of the three-dimensional reconstruction of the target element on a display;
   wherein the iterative reconstruction algorithm is applied using cone-beam forward projection and back projection.

2. A method according to claim 1, wherein the radiation absorbance images are acquired by transmitting x-ray energy from an x-ray source through the target element to an x-ray detector.

3. A method according to claim 2, wherein the x-ray detector is a digital x-ray detector having a plurality of detector pixels.

4. A method according to claim 3, wherein the three-dimensional reconstruction of the target element is represented as an array of voxels having a uniform or non-uniform size in three-dimensions.

5. A method according to claim 4, wherein a forward projection step is implemented by ray tracing from the x-ray source to a detector pixel and the forward projection of the target element is obtained by repeating the ray tracing for each detector pixel to calculate an attenuation value for each voxel.

6. A method according to claim 5, wherein a back projection step is implemented by locating detector pixels containing attenuation information relating to a selected voxel and using those pixels to update the attenuation value of the selected voxel.

7. A method according to claim 6, wherein the back projection step includes performing a back projection for at least each voxel corresponding to a three-dimensional reconstruction of the target element.

8. A method according to claim 1, wherein radiation absorbance images are acquired through a number of angles that is less than or equal to about 100.

9. A method according to claim 1, wherein radiation absorbance images are acquired through a range of angles that is limited to only between about 30 and 120 degrees.

10. A method according to claim 1, wherein the iterative reconstruction algorithm is a maximum likelihood algorithm.

11. A method according to claim 10, wherein the maximum-likelihood estimation is implemented using an expectation-maximization algorithm.

12. A method according to claim 1, wherein the target element is at least a portion of a human patient.

13. A method according to claim 12, wherein the target element is a breast of a female human patient.

14. A method according to claim 1, wherein a number of iterations is less than or equal to about 10.

15. A system for three-dimensional imaging of a target element comprising:
   an image acquisition element for obtaining a plurality of images of the target element from a plurality of angles having:
   a radiation source positionable at a plurality of angles with respect to the target element; and
   a radiation detector positioned so as to detect radiation emitted by the radiation source passing through the target element and determine a plurality of attenuation values for radiation passing through the target element to establish a radiation absorbance projection image of the target element for a particular radiation source angle; and
   a processor configured to apply an iterative reconstruction algorithm to radiation absorbance projection images of the target element obtained from a plurality of radiation source angles to generate a three-dimensional reconstruction of the target element using tomosynthesis, wherein the iterative reconstruction algorithm is applied using cone-beam forward projection and back projection.

16. A system according to claim 15, wherein the radiation detector is a digital x-ray detector having a plurality of detector pixels.

17. A system according to claim 16, wherein the three-dimensional reconstruction of the target element is represented as an array of voxels having a uniform or non-uniform size in three-dimensions.

18. A system according to claim 17, wherein a forward projection step is implemented by ray tracing from the radiation source to a detector pixel and the forward projection of the target element is obtained by repeating the ray tracing for each detector pixel to calculate an attenuation value for each voxel.

19. A system according to claim 18, wherein a back projection step is implemented by locating detector pixels containing attenuation information relating to a selected voxel and using those pixels to update the attenuation value of the selected voxel.

20. A system according to claim 19, wherein the back projection step includes performing a back projection for at least each voxel corresponding to a three-dimensional reconstruction of the target element.

21. A system according to claim 15, wherein radiation absorbance projection images are acquired through a number of angles that is less than or equal to about 100.

22. A system according to claim 15, wherein radiation absorbance projection images are acquired through a range of angles that is limited to only between about 30 and 120 degrees.

23. A system according to claim 15, wherein the iterative reconstruction algorithm is a maximum likelihood algorithm.

24. A system according to claim 23, wherein the maximum-likelihood estimation is implemented using an expectation-maximization algorithm.

25. A computer-readable medium encoded with a computer program for three-dimensional imaging of a target element from a plurality of radiation absorbance projection images obtained at different angles from an image acquisition element having a radiation source positionable at a plurality of angles with respect to the target element and a radiation detector positioned so as to detect radiation emitted by the radiation source passing through the target element and determine a plurality of attenuation values for radiation passing through the target element to establish a radiation absorbance projection image of the target element for a particular radiation source angle, the computer program code comprising:

computer program code for applying an iterative reconstruction algorithm to the radiation absorbance projection images of the target element obtained from a plurality of radiation source angles to generate the three-dimensional reconstruction of the target element using tomosynthesis and displaying at least a portion of the three-dimensional reconstruction of the target element, wherein the iterative reconstruction algorithm is applied using cone-beam forward projection and back projection.

26. A computer-readable medium encoded with a computer program according to claim 25, wherein the radiation detector is a digital x-ray detector having a plurality of detector pixels.

27. A computer-readable medium encoded with a computer program according to claim 26, wherein the three-dimensional reconstruction of the target element is represented as an array of voxels having a uniform or non-uniform size in three-dimensions.

28. A computer-readable medium encoded with a computer program according to claim 27, wherein a forward projection step is implemented by ray tracing from the radiation source to a detector pixel and the forward projection of the target element is obtained by repeating the ray tracing for each detector pixel to calculate an attenuation value for each voxel.

29. A computer-readable medium encoded with a computer program according to claim 28, wherein a back projection step is implemented by locating detector pixels containing attenuation information relating to a selected voxel and using those pixels to update the attenuation value of the selected voxel.

30. A computer-readable medium encoded with a computer program according to claim 29, wherein the back projection step includes performing a back projection for at least each voxel corresponding to a three-dimensional reconstruction of the target element.

31. A computer-readable medium encoded with a computer program according to claim 25, wherein radiation absorbance projection images are acquired through a number of angles that is less than or equal to about 100.

32. A computer-readable medium encoded with a computer program according to claim 25, wherein radiation absorbance projection images are acquired through a range of angles that is limited to only between about 30 and 120 degrees.

33. A computer-readable medium encoded with a computer program according to claim 25, wherein the iterative reconstruction algorithm is a maximum likelihood algorithm.

34. A computer-readable medium encoded with a computer program according to claim 33, wherein the maximum-likelihood estimation is implemented using an expectation-maximization algorithm.

* * * * *